United States Patent
Yasuda et al.

(10) Patent No.: US 6,245,207 B1
(45) Date of Patent: Jun. 12, 2001

(54) CELL SEPARATION DEVICE USING ULTRASOUND AND ELECTROPHORESIS

(75) Inventors: Kenji Yasuda, Hiki-gun; Takeshi Sakamoto, Asaka, both of (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/313,212

(22) Filed: May 18, 1999

(30) Foreign Application Priority Data

May 20, 1998 (JP) ................................... 10-137924

(51) Int. Cl.$^7$ ............... C02F 1/40; C02F 11/00; C25B 9/11; C25B 11/00

(52) U.S. Cl. ............... 204/600; 204/157.42; 422/186.04; 422/255

(58) Field of Search ............... 422/186.04, 255; 204/600, 450, 157.42

(56) References Cited

U.S. PATENT DOCUMENTS

| | | |
|---|---|---|
| 4,743,361 | 5/1988 | Schram . |
| 5,225,089 | 7/1993 | Benes . |
| 5,277,774 * | 1/1994 | Shmidt et al. ................ 204/545 |

FOREIGN PATENT DOCUMENTS

| | | |
|---|---|---|
| 6-241977 | 9/1994 | (JP) . |
| 7-47259 | 2/1995 | (JP) . |

OTHER PUBLICATIONS

Annals New York Academy Of Science, 1983, "Surface Charge of Old, Transformed, and Experimentally Deteriorated Erythrocytes", D. Danon et al, pp. 149–158, No month avail.

Mechanisms Of Aging And Development, vol. 24, No. 1, Jan. 1984, "Aging of the Erythrocyte. XIX. Decrease In Surface Charge Density Of Bovine Erythrocytes", G. Bartoz et al, pp. 1–7.

Journal Of Acoustical Society America, 1991, vol. 89, "Acoustical Tweezers", J. Wu, pp. 2140–2143, No month avail.

Acustica, vol. 5, 1955, "Acoustic Radiation Pressure On A Compressible Sphere", K. Yosioka et al, pp. 167–178, No month avail.

Journal Of Acoustical Society Of America, vol. 91, No. 6, Jun. 1992, "Separation devices based on forced coincidence response of fluid–filled pipes", T. Tolt et al, pp. 3152–3156.

* cited by examiner

Primary Examiner—Kathryn Gorgos
Assistant Examiner—Wesley A. Nicolas
(74) Attorney, Agent, or Firm—Mattingly, Stanger & Malur, P.C.

(57) ABSTRACT

A cell separation module for separating and collecting cells having a charge and cells having no charge comprises a holder and a throwaway cell separation chamber held by the holder. Ultrasound is introduced into the cell separation chamber so as to allow force for causing cells to be put together to act into the cell separation chamber. In addition, an electrostatic force is allowed to act in the cell separation chamber so as to cause the cell to move by the charges of the cells. Competition between both the forces is used to separate the cells correspondingly to the freshness of the cells.

1 Claim, 5 Drawing Sheets

CELL SEPARATION DEVICE USING ULTRASOUND AND ELECTROPHORESIS

BACKGROUND OF THE INVENTION

The present invention relates to a cell separation device using competition between electrostatic force and acoustic radiation force.

It is in general known that a cell has a negative charge on its surface and the charge is gradually reduced by a decrease in its living activity. For example, in an electric field erythrocytes are subjected to electrophoresis toward an anode caused by the negative charge of their surface. At this time, the mobility of the erythrocytes is not uniform and different depending on the surface condition of the respective erythrocytes. The causes thereof are thought to be different freshness of the respective erythrocytes and relevance with disease symptoms. The change in the charge which erythrocytes have were introduced in, for example, Donon D et al., Ann N Y Acad Sci 1983; 149–458, "Surface Charge of Old, Transformed, and Experimentally Deteriorated Erythrocytes", or Bartosz G et al., Mech. "Ageing Dev January 1984: 24(1) 1–7 Aging of the Erythrocyte. XIX. Decrease in Surface Charge Density of Bovine Erythrocytes."

It has been known since the 19th century that particles in a fluid can be trapped without contact by ultrasonic irradiation. Concerning the acoustic radiation force which particles receive when the radiation force acts on the particles, for example, in Acoust. Soc. Am. 89(1991) pp. 2140–2143, J. Wu, reported that he succeeded in trapping polystyrene spheres of 270 μm diameter at the focal point of focal ultrasound. As regards the principle that particles are trapped by acoustic radiation force, in Acoustica 5 (1955) pp. 167–178, K. Yosioka and Y. Kawasima reported that they calculated the intensity, in a perfect fluid, of the acoustic radiation force which particles receive in a standing wave and a traveling wave, and the acoustic radiation force that the particles floating in the standing wave receive is in proportion to the volume of the particles and the frequency of the ultrasound forming the standing wave. Furthermore, Japanese Patent laid open No. 7-47259, proposed by the present inventors, discloses a manner of introducing ultrasound into a tube in which a fluid is allowed to flow so as to focus particles continuously within some area, or a method for collecting the focused particles. Furthermore, Japanese Patent laid open No. 6-241977 by the inventors discloses a particle separation device for separating and collecting particles having different particle sizes and made of different materials by the competition acoustic radiation force and other non-contact force such as electrostatic force.

It has been known heretofore that as the frequency of ultrasound used in a standing wave is gradually changed, the position of nodes of the standing wave changes accordingly and particles also move. In J. Acoust. Soc. Am. 91(1992), pp. 3152–3156, T. L. Tolt et al. reported a means for moving and concentrating actual particles trapped in nodes of a standing wave by sweeping, upwards and downwards, the frequency of ultrasound introduced into a fluid wherein the particles are dispersed. Furthermore, U.S. Pat. No. 5,225,089 by E. Benes et al. discloses a means for concentrating particles by raising the frequency of ultrasound radiated from an ultrasound source arranged in a channel.

Moreover, it has also been known heretofore that the position of nodes of a standing wave can be controlled by controlling the phases of ultrasound radiated from a plurality of different ultrasound sources for generating a superimposed waveform, for example, as proposed by the present inventor Yasuda et al. in U.S. patent application Ser. No. 08/745,656. U.S. Pat. No. 4,743,361 by C. J. Schram discloses a means of applying this technique actually to measure physical properties of particles by observing how much the particles follow the movement of the position of nodes of a standing wave. It has also been known heretofore that when ultrasound having slightly different frequencies are radiated oppositely, the position of nodes of a generated standing wave advances by the slight difference between the frequencies.

SUMMARY OF THE INVENTION

The cell separation techniques using a surface charge of cells in the prior art have an advantage that the cells can be separated and analyzed without dyeing. Moreover, the difference between mobilities in electrophoresis is used to separate the cells, and thus the techniques are suitable for analyzing a very small amount of a sample in a batch processing manner. However, they are not suitable for continuos separation of a large amount of a cell sample.

An object of the present invention is to provide a cell separation device for separating and collecting fresh cells having a charge effectively and continuously without dyeing by using competition between acoustic radiation force and electrostatic force.

To attain the above-mentioned object, the cell separation device causes separation of cells in accordance with their freshness by using two different forces of a force acting on the cells by ultrasound radiated from opposite side faces of a tube, that is, a force causing the cells to be put together toward the center of the tube or a force causing the cells to advance perpendicularly to the advancing direction of a sample fluid, and an electrostatic force acting on the cells from the opposite side faces of the tube, that is, a force causing the cells to move in the direction of the gradient of electric field on the basis of the charges of the cells.

DESCRIPTION OF THE PREFERRED EMBODIMENT

Figure 1:
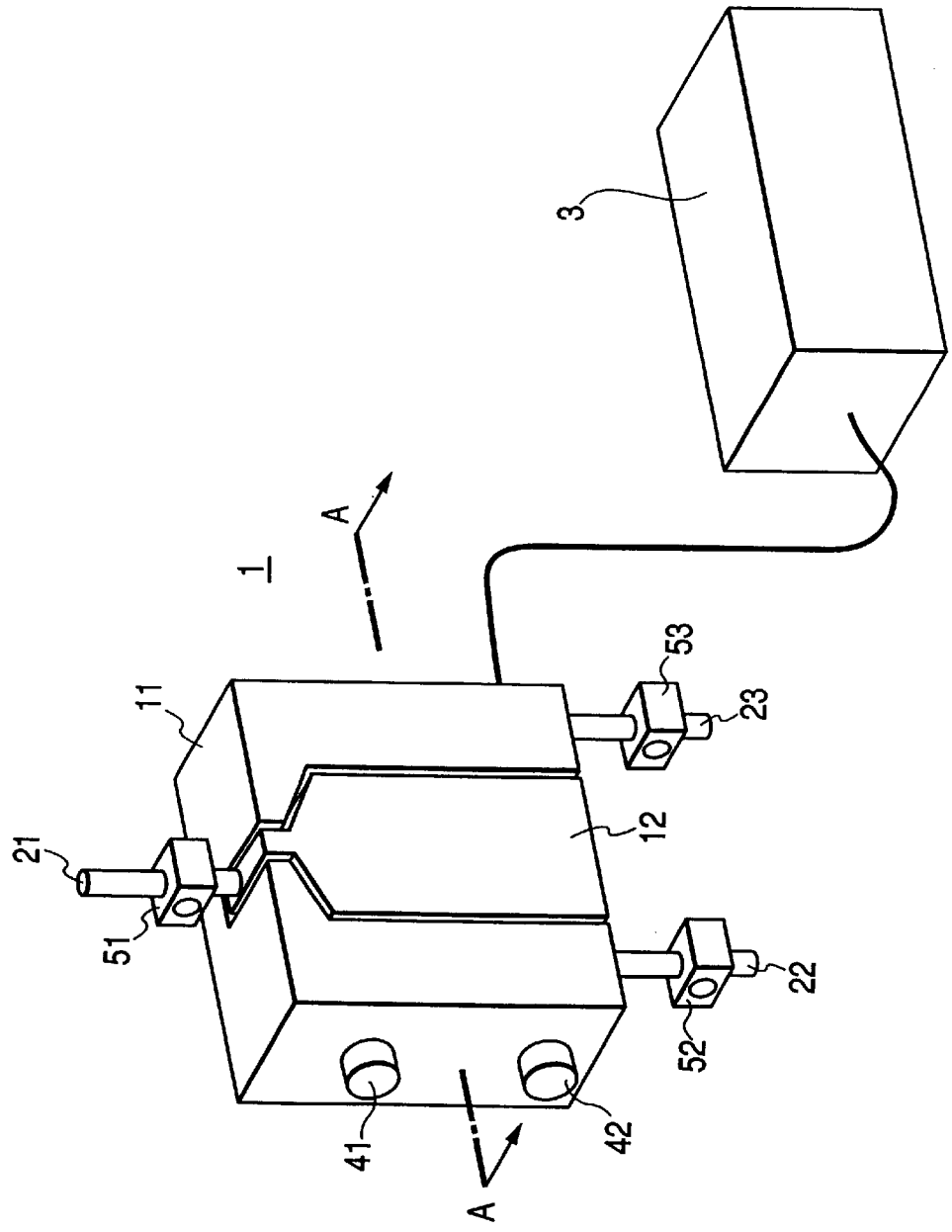
FIG. 1 is a perspective view illustrating the whole structure of a cell separation device of the present invention.

The whole structure of a cell separation device of the present invention will be described, referring to FIG. 1, which is a perspective view. In FIG. 1, reference numeral 1 represents a cell separation module for separating and collecting cells having different charges. The module comprises a throwaway cell separation chamber 12 and a holder 11 which holds the cell separation chamber 12 from which and which the chamber 12 can easily be put on and taken off. Reference numeral 3 represents a voltage control circuit for controlling voltages applied to ultrasound sources and electrode plates. Reference numeral 21 represents an introducing tube for introducing a sample solution containing cells into the separation chamber 12, and reference numerals 22 and 23 represent collecting tubes for collecting separated samples. Reference numerals 51, 52 and 53 represent valves attached to the tubes 21, 22 and 23, respectively, which are valves for adjusting the flowing amounts in the respective tubes. Unillustrated pumps for producing streams of the sample solution are attached to the respective tubes 21, 22 and 23.

Figure 2:
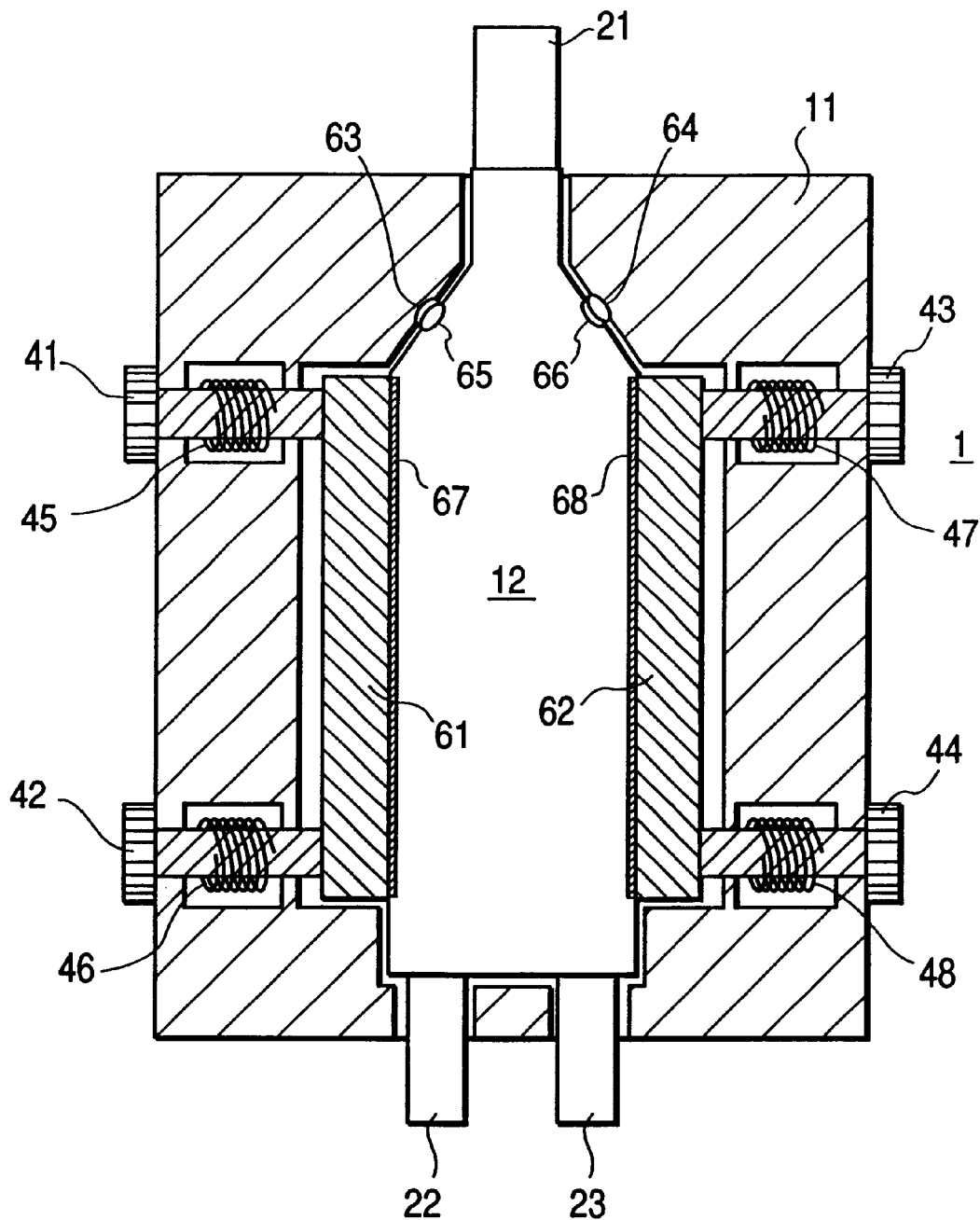
FIG. 2 is a cross section taken on line A—A of the cell separation module shown in FIG. 1, which is viewed in the direction of the arrows.

FIG. 2 is a cross section taken on line A—A of the cell separation module 1 shown in FIG. 1, which is viewed in the direction of the arrows. The cell separation chamber 12 can be put on and taken off from the cell holder 11. When different chambers are used, contamination can be avoided by exchanging the cell separation chamber 12, as well as the introducing tube 21, the collecting tubes 22 and 23. When the cell separation chamber 12 is installed in the cell holder 11, the chamber 12 is brought into close contact with ultrasound sources 61 and 62 by fasteners 41, 42, 43 and 44, to which springs 45, 46, 47 and 48 are fitted, respectively. Thus, the ultrasound generated by the ultrasound sources 61 and 62 can be introduced into the cell separation chamber 12.

Electrode plates 67 and 68 are oppositely arranged on the inner face of the cell separation chamber 12. Contacts 65 and 65 are electrically connected to the electrode plates 67 and 68, and are also arranged on the inner face of the chamber 12. Contacts 63 and 64 are arranged on the cell holder 11 to oppose the positions of these contacts 65 and 66. These contacts 63 and 64 are connected to a given voltage source in the voltage control circuits 3. Therefore, when the cell separation chamber 12 is put on the cell holder 11, the contacts 63 and 64 are naturally brought into contact with the contacts 65 and 66 so that a given voltage is applied to the electrode plates 67 and 68 in the cell separation chamber 12. It is desirable that the cell separation chamber 12 is made of a raw material that can easily be burned, such as a combustible plastic. A lubricant such as silicone grease may be applied to the contact points of the ultrasound sources 61/62 and the cell separation chamber 12 to promote the transmission of ultrasound. It is desirable that the internal diameter of the tubes 21, 22 and 23 and the tube 12 be 1 mm or larger, in order to prevent clogging due to clotting of blood.

In FIG. 2, illustrating the portions at which the collecting tubes 22 and 23 are jointed to the cell separation chamber 12 is omitted. This is because these portions are different in their structures in accordance with the forms of embodiments which will be described later.

Figure 3:
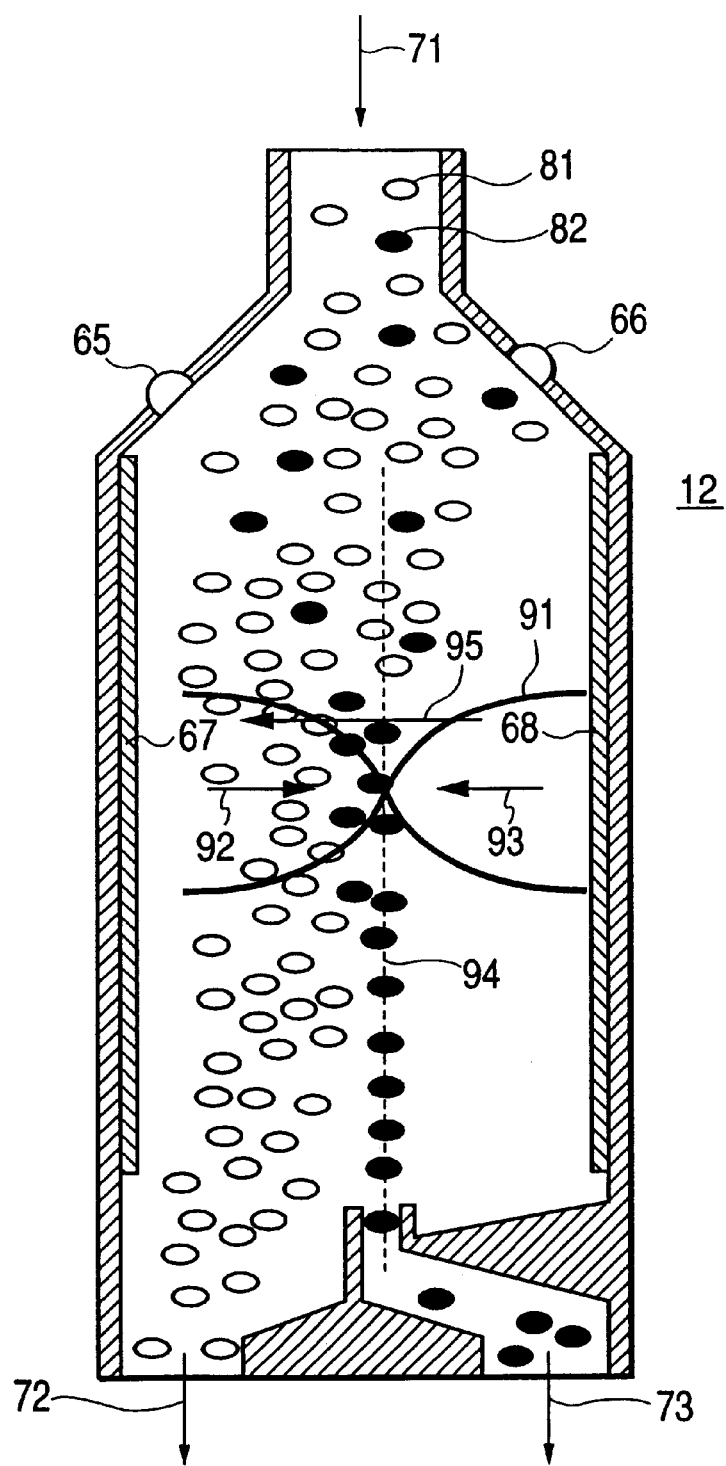
FIG. 3 is a schematic view of a first method for separating cells, giving, as an example, separation of erythrocyte components in a sample solution.

FIG. 3 is a schematic view of a first method for separating cells, giving, as an example, separation of erythrocyte components in a sample solution. The sample solution containing the erythrocytes, introduced into the chamber 12 in the direction of an arrow 71, is influenced in the chamber 12 by two sorts of non-contact forces. One is an acoustic radiation force based on the ultrasound generated by the ultrasound sources 61 and 62 and are introduced into the cell separation chamber 12. In the example shown in FIG. 3, the acoustic radiation force is adjusted so that the width of the inner wall of the rectangular parallelepiped tube becomes ($\lambda/2$), wherein $\lambda$ is the wavelength of the ultrasound. Both of erythrocytes 81 and 82 in the sample solution receive non-contact forces 92 and 93 toward a node 94 of acoustic pressure at the center of the tube by a standing wave 91 generated by the ultrasound.

In the case that the electrode plates 67 and 68 arranged on the opposite faces of the rectangular parallelepiped tube 12 make an anode and a cathode, respectively, the erythrocytes also receive an electrostatic force, which is the other non-contact force, in the direction of an arrow 95. As the freshness of the erythrocytes drops, the quantity of the charge of the erythrocytes decreases. Thus, in the case of erythrocytes just before hemolysis, the erythrocytes have substantially no charge. The erythrocytes 81 having a higher freshness approach the electrode plate 67 more greatly, and the erythrocytes 82 having a higher probability of hemolysis approach the position 94 of the acoustic pressure node of the standing wave more greatly. In FIG. 3, the highly fresh erythrocytes 81 are represented by white dots, and the erythrocytes 82 having a high probability of hemolysis are represented by black dots. As shown by these dots, if only the erythrocytes 82 at the downstream side of the stream and near the position of the acoustic pressure node of the standing wave at the tube center are collected and removed along an arrow 73, the sample solution containing the highly fresh erythrocytes 81 can be obtained along an arrow 72.

In the present embodiment, either one of the electrodes 67 and 68 attracts components which are other than the erythrocytes and which are contained in the sample solution and have a charge. Thus, these components are collected together with the highly fresh erythrocytes 81. Therefore, the present embodiment has an advantage that only one part of the solution that does not contain the components having a charge in the sample solution flows out together with the erythrocytes 82 having a high probability of hemolysis.

Figure 4:
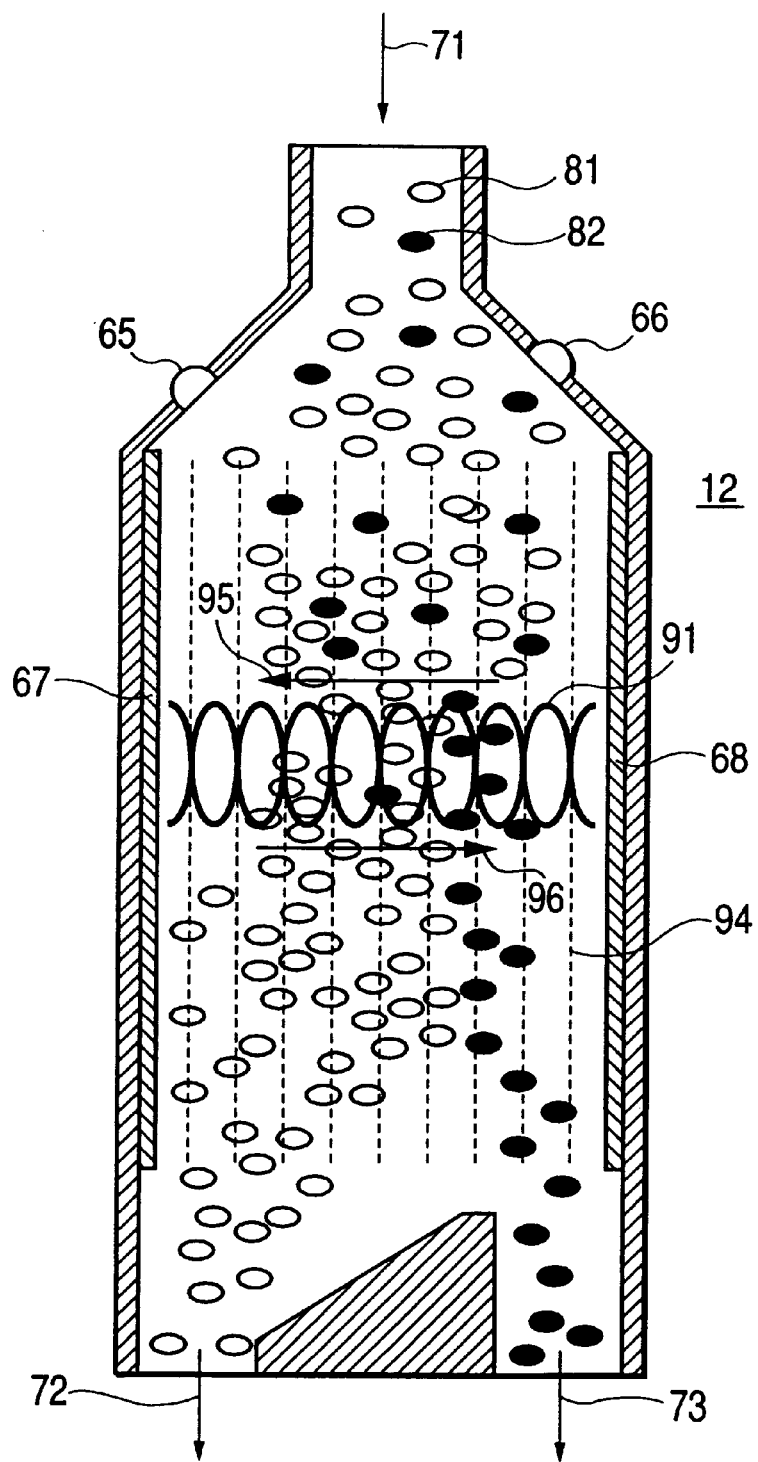
FIG. 4 is a schematic view of a second method, giving, as an example, separation of erythrocyte components in a sample solution.

FIG. 4 is a schematic view of a second method, giving separation of erythrocyte components in a sample solution, as an example. In the present embodiment, a voltage is applied to electrodes by the voltage control circuit 3 so that the directions of wave numeral vectors of ultrasound generated by the ultrasound sources 61 and 62 and introduced into the cell separation chamber 12 become reverse by 180°. When the following ultrasound (the following equation 1 and 2) is radiated from the ultrasound sources 61 and 62, respectively, a standing wave in the tube can be represented by the following equation (3):

$$A \cdot \sin[(\omega+\Delta\omega)\cdot t - k\cdot x] \quad \text{(equation 1)}$$

$$A \cdot \sin[(\omega+\Delta\omega)\cdot t + k\cdot x] \quad \text{(equation 2)}$$

$$\{2A \cos[(\Delta\omega\cdot t - kx)]\}\cdot \sin(\omega\cdot t) \quad \text{(equation 3)}$$

In these equations, $\omega$ and $\Delta\omega$ are the angular frequencies of the ultrasound from the two sources, and A is the peak pressure thereof. Accordingly, the node or the loop of the generated standing wave 91 advances toward the ultrasound source 62 as shown by an arrow 96 at the speed of the following:

$$\frac{\Delta\omega}{k} \quad \text{(equation 4)}$$

Therefore, the erythrocytes dispersed in the sample solution also advance toward the electrode 68 after they are trapped in the node of the standing wave. In the case that the electrodes 67 and 68 arranged on the opposite faces of the rectangular parallelepiped tube 12 make an anode and a cathode, respectively, the erythrocytes also receive an electrostatic force, which is the other non-contact force, in the direction of an arrow 95. In the same way as in FIG. 3, as the freshness of the erythrocytes drops, the quantity of the charge of the erythrocytes decreases. Thus, in the case of erythrocytes just before hemolysis, the erythrocytes have substantially no charge. For this reason, the erythrocytes 81 having a higher freshness (represented by white dots in the same way as in FIG. 3) approach the electrode plate 67 more greatly, and the erythrocytes 82 having a higher probability of hemolysis (represented by black dots in the same way as in FIG. 3) approach the electrode plate 68. Therefore, if only the erythrocytes 82 at the downstream side of the stream and near the electrode plate 68 are collected and removed along the arrow 73, the sample solution containing highly fresh erythrocytes 81 can be obtained along the arrow 72.

Figure 5:
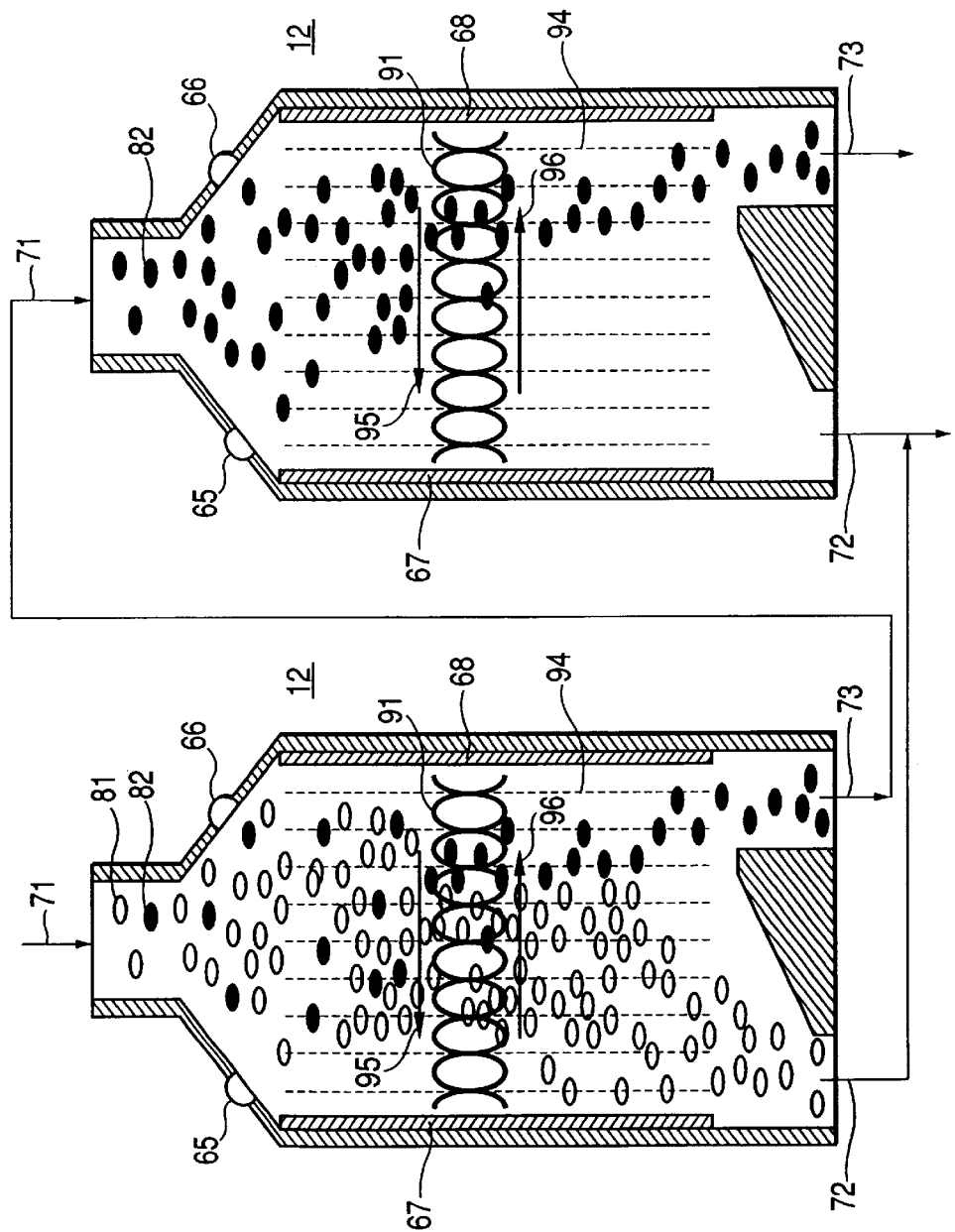
FIG. 5 is a schematic view illustrating important elements of an improved embodiment of the cell separation shown in FIG. 4.

In the present embodiment, either one of the electrodes 67 and 68 also attracts components which are other than the erythrocytes and which are contained in the sample solution and have a charge. Among these, the components that the electrode 67 attracts are collected together with the highly fresh erythrocytes 81. However, the components that the electrode 68 attracts are collected together with the erythrocytes having a deteriorated freshness. Thus, if these components are abolished, a part of the useful components in the sample solution is also abolished. For this reason, in the present embodiment, as FIG. 5 shows only a cascade arrangement of the cell separation chamber 12, it is effective that the sample solution collected along the arrow 73 is treated by adding another cell separation module 1 and reversing the polarities of the electrodes 67 and 68.

In this way, the erythrocytes 82 which are not fresh in the sample solution collected along the arrow 73 are collected along the arrow 73 in the same manner as in FIG. 4. However, the components having a charge in the sample solution are collected along the arrow 72 since the voltage polarities of the electrodes 67 and 68 are reversed. As a result thereof, if the sample solutions from the arrow 72 side of the two cell separation modules 1 are put together, it is possible to obtain a sample solution containing the highly fresh erythrocytes 81 which are the same as in FIG. 3. From the arrow 73 side of the rear cell separation module 1, only a part of the solution that does not contain the components having a charge flows out together with the erythrocytes 82 having a high probability of hemolysis.

However, in the case that, for example, only stored erythrocytes are transfused, only the erythrocytes are diluted with a physiological salt solution and transfused. In this case, it is sufficient to check the freshness of the transfused erythrocytes. Thus, even in the case of the embodiment shown in FIG. 4, any cascade structure is not necessary.

In this case, it is desirable to use, as the frequency of the ultrasound generated by the ultrasound source, a frequency having a sufficiently shorter wavelength than the width of the area for generating a standing wave in the tube. In order to suppress the generation of cavitation which may damage the sample, the used frequency should be a frequency of 500 kHz or higher. This is because the peak pressure $P_c$ of the cavitation area of the ultrasound has the following relationship with the frequency f of the used ultrasound.

$$P_c f^{1.2}$$ (equation 5)

As described in detail above, the present invention has an advantage that the necessity for dyeing of or contacting with a sample solution are eliminated when cells in the sample solution can be continuously separated and collected in accordance with the freshness of the cells.

What is claimed is:

1. A cell separation device comprising:

a rectangular parallelepiped tube arranged to allow a sample solution containing cells having different charges to be separated correspondingly to said charges of said cells to flow;

an inlet from which the sample solution containing said cells is introduced into said rectangular parallelepiped tube;

a pair of ultrasound sources, each of which contacts an opposite outer surface of said rectangular parallelepiped tube, wherein ultrasound waves generated from said pair of ultrasound sources transmit an acoustic radiation force on said cells and cause said cells having substantially no charge to move toward a center of flow of said sample solution in a direction perpendicular to the flow of said sample solution;

an anode electrode plate and a cathode electrode plate, each arranged on a different inner opposite surface of said rectangular parallelepiped tube, wherein each of said ultrasound sources faces a different one of said anode electrode plate and said cathode electrode plate, and said anode electrode plate and said cathode electrode plate transmit an electrostatic force generated by applying a non-alternating electric field on said cells and cause said cells each having a charge to move toward one of said anode electrode plate and said cathode electrode plate and away from the center of flow of said sample solution, in the direction perpendicular to the flow of said sample solution;

an ultrasound generation control unit arranged to cause the respective ultrasound sources to generate ultrasound waves so as to generate a standing wave of ½ wavelength, wherein a width of the inner opposite surface of said rectangular parallelepiped tube is equal to the ½ wavelength;

a power source circuit unit arranged to generate potential difference between said anode electrode plate and said cathode electrode plate;

a first outlet from which said cells having substantially no charge and coming together by the acoustic radiation force to the center of the flow of said sample solution flow out; and a second outlet from which said cells, each being separated continuously by competition between the acoustic radiation force and the electrostatic force and each having a charge coming together to one of said anode electrode plate and said cathode electrode plate, flow out.

* * * * *